(12) United States Patent
Lai et al.

(10) Patent No.: US 7,234,936 B2
(45) Date of Patent: Jun. 26, 2007

(54) ORTHODONTIC SYSTEMS WITH RESILIENT APPLIANCES

(75) Inventors: Ming-Lai Lai, Arcadia, CA (US); Tsi-Zong Tzou, Arcadia, CA (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 10/983,457

(22) Filed: Nov. 8, 2004

(65) Prior Publication Data
US 2006/0099544 A1 May 11, 2006

(51) Int. Cl.
*A61C 3/00* (2006.01)
(52) U.S. Cl. .............................. 433/20; 433/6
(58) Field of Classification Search .................. 433/6, 433/24, 20
See application file for complete search history.

(56) References Cited

U.S. PATENT DOCUMENTS

| | | | |
|---|---|---|---|
| 4,248,588 A | 2/1981 | Hanson | |
| 4,492,573 A | 1/1985 | Hanson | |
| 4,712,999 A | 12/1987 | Rosenberg | |
| 4,954,080 A | 9/1990 | Kelly et al. | |
| 4,983,334 A * | 1/1991 | Adell | 264/16 |
| 5,055,039 A | 10/1991 | Abbatte et al. | |
| 5,445,770 A | 8/1995 | Adam et al. | |
| 5,506,300 A | 4/1996 | Ward et al. | |
| 5,645,420 A | 7/1997 | Bergersen | |
| 5,711,666 A | 1/1998 | Hanson | |
| 5,882,192 A | 3/1999 | Bergersen | |
| 5,975,893 A | 11/1999 | Chishti et al. | |
| 6,183,248 B1 | 2/2001 | Chishti et al. | |
| 6,299,440 B1 * | 10/2001 | Phan et al. | 433/24 |
| 6,302,688 B1 | 10/2001 | Jordan et al. | |
| 6,388,043 B1 | 5/2002 | Langer et al. | |
| 6,450,807 B1 | 9/2002 | Chishti et al. | |
| 6,524,101 B1 | 2/2003 | Phan et al. | |
| 6,582,225 B1 | 6/2003 | Bergersen | |
| 6,582,226 B2 | 6/2003 | Jordan et al. | |
| 6,607,382 B1 | 8/2003 | Kuo et al. | |
| 6,648,638 B2 | 11/2003 | Castro et al. | |
| 6,722,880 B2 | 4/2004 | Chishti et al. | |
| 6,783,360 B2 | 8/2004 | Chishti | |
| 2001/0041320 A1* | 11/2001 | Phan et al. | 433/6 |

(Continued)

FOREIGN PATENT DOCUMENTS

DE 32 32 550 2/1984

(Continued)

OTHER PUBLICATIONS

Pending U.S. Appl. No. 10/865,649, filed Jun. 10, 2004.

(Continued)

*Primary Examiner*—Cary E. O'Connor
(74) *Attorney, Agent, or Firm*—James D. Christoff

(57) ABSTRACT

Systems for moving teeth of a patient's dental arch from a first tooth arrangement to a second tooth arrangement include a plurality of resilient appliances such as positioning trays or elongated arch members that are used in sequence. Each appliance of the systems includes a row of spaced apart couplings for connection to respective teeth of the dental arch. The appliances have certain geometric characteristics that match the geometric characteristics of other appliances of the system, and at least one appliance has a stiffness that is greater than the stiffness of at least one other appliance.

7 Claims, 4 Drawing Sheets

U.S. PATENT DOCUMENTS

| | | |
|---|---|---|
| 2003/0055198 A1 | 3/2003 | Langer et al. |
| 2003/0157454 A1 | 8/2003 | Hansen et al. |
| 2003/0207224 A1 | 11/2003 | Lotte |
| 2004/0142299 A1 | 7/2004 | Miller |
| 2004/0209218 A1 | 10/2004 | Chishti et al. |

OTHER PUBLICATIONS

*Straight Wire, The Concepts and Appliance*, by Lawrence F. Andrews, L.A. Wells Co., copyright 1989, chapter 3, pp. 13-24.

ASTM Test Method D412-98a; Standard Test Method for Vulcanized Rubber and Thermoplastic Elastomers-Tension.

ASTM Test Method D882-02; Standard Test Method for Tensile Properties of Thin Plastic Sheeting.

*Viscoelastic Properties of Polymers*, by John D. Ferry, third edition, John Wiley and Sons, Inc., copyright 1980, pp. 1-32.

*The Use of Tooth Thickness in Predicting Intermaxillary Tooth-Size Discrepancies*, Rudolph et al., The Angle Orthodontist 1998, No. 2, pp. 1-14.

Bolton Analysis for Tooth Size Discrepancies, Overall Assessment (6-6), 2003 CSLaw, UCLA Pedo/UCLA Ortho.

*Evaluation of the Validity of Tooth Size and Arch Width Measurements Using Conventional and Three-Dimensional Virtual Orthodontic Models*, Zilberman et al., The Angle Orthodontist, vol. 73, No. 3, 2003, pp. 301-306.

Pending U.S. Appl. No. 10/983,795, filed Nov. 8, 2004.

* cited by examiner

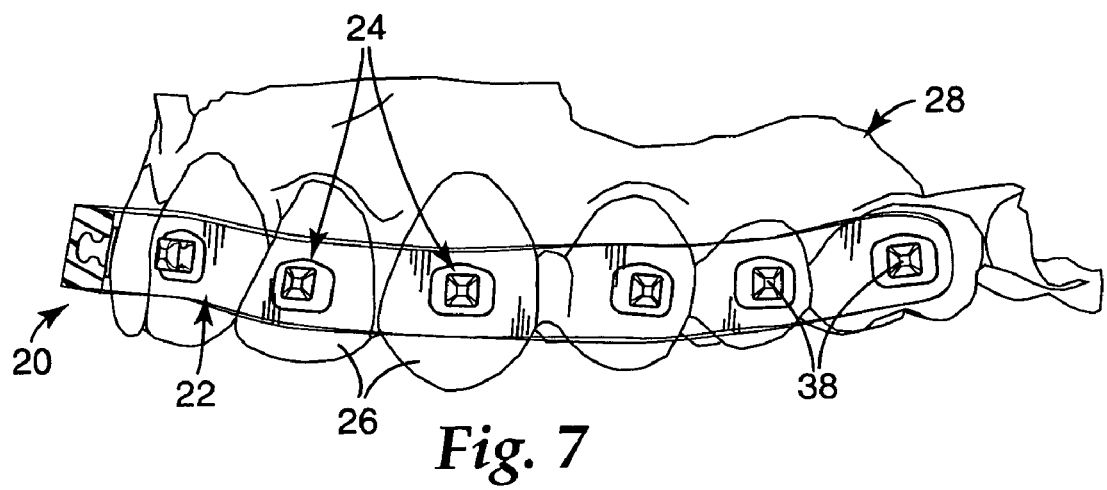
Fig. 7
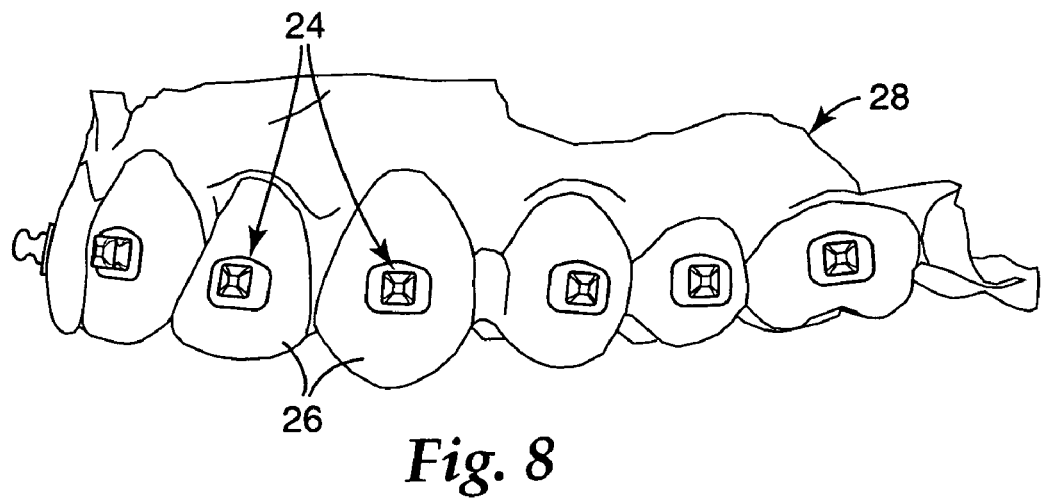
Fig. 8
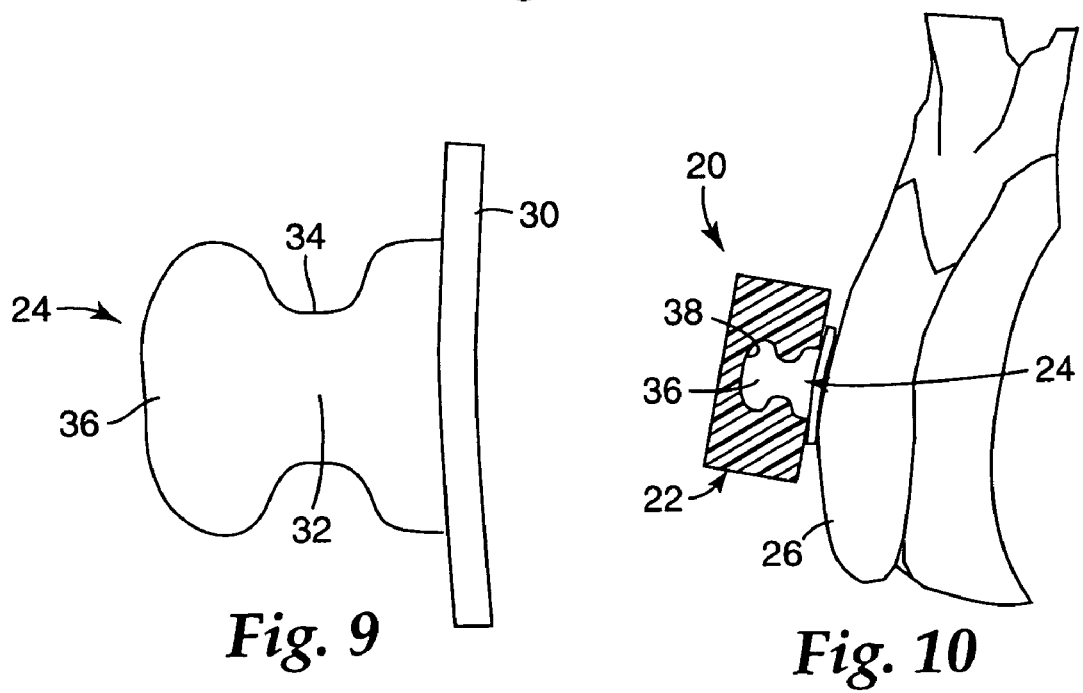
Fig. 9
Fig. 10

ORTHODONTIC SYSTEMS WITH RESILIENT APPLIANCES

BACKGROUND OF THE INVENTION

1. Field of the Invention

This invention relates to orthodontic treatment systems wherein resilient appliances are used in sequence to move the patient's teeth to desired orientations in the dental arch.

2. Description of the Related Art

Orthodontic treatment involves movement of malpositioned teeth to improved orientations. Orthodontic treatment can greatly enhance the aesthetic appearance of the patient's teeth, especially in regions near the front of the oral cavity. Orthodontic treatment can also improve the patient's occlusion so that the teeth function better with each other during mastication.

One type of orthodontic treatment is carried out by the use of elastomeric positioning appliances, also known as repositioning trays or alignment trays. These appliances have overall, generally "U"-shaped configuration that generally matches the shape of the patient's dental arch, and a row of receptacles in the appliance receive respective teeth of the dental arch. Some patients favor elastomeric positioning appliances because they can be removed while eating.

Elastomeric positioning appliances are often made by first taking an impression of the patient's dental arches and then making a plaster of Paris or "stone" model from the impression. Next, the teeth of the stone model representing the teeth to be moved during treatment are cut or sawn from remaining portions of the model and repositioned as desired, using a wax or other material to hold the repositioned teeth in place. A sheet of thermoplastic material is then placed over the model and heated such that the sheet is formed into the exact shape of the model with the repositioned teeth. Subsequently, edges of the sheet are trimmed as desired to form a tray. When the tray is set in place over the patient's dental arch, the elastic characteristics of the thermoplastic material tend to move the teeth toward the orientations as represented by the repositioned teeth of the model.

A system of elastomeric positioning appliances available from Align Technology, Inc. of Santa Clara, Calif. involves a series of alignment trays that are used in sequence. The trays are custom-made for each patient, and each tray is constructed to move the teeth along an incremental portion of the treatment path. One possible method of making such positioning trays is somewhat similar to the method described above, except that a model is provided for each tray of the series and the teeth are repositioned on each model in accordance with the intended incremental positions of the patient's teeth along the desired treatment path.

Another type of orthodontic treatment is carried out by the use of a series of tiny, slotted brackets, each of which is affixed to a respective tooth of the patient's dental arch. A resilient arch member such as a curved, elongated archwire is placed in the slot of each bracket. Ends of the archwire are often received in devices known as buccal tubes that are affixed to the patient's molar teeth. The archwire serves as a track to guide movement of the teeth to desired positions.

SUMMARY OF THE INVENTION

The present invention is directed to novel systems of orthodontic appliances that include a series of resilient appliances for use in sequence. Each appliance of the series is constructed to move the teeth toward desired positions and may optionally have a geometry identical to the geometry of other appliances of the system. However, at least one of the appliances is constructed to provide a greater amount of force per unit displacement of tooth movement on at least some of the teeth than other appliances of the series in order to more efficiently move the teeth to their final positions as the end of the treatment program is approached.

In more detail, the present invention in one aspect is directed toward a system for moving teeth of a patient's dental arch from a first tooth arrangement to a second tooth arrangement comprising a plurality of resilient appliances. Each appliance has a row of spaced apart couplings for connection to respective teeth of the dental arch. Each of the couplings of each appliance is arranged in a certain relative orientation with respect to the remaining couplings of the same appliance when the appliance is relaxed. The relative orientation of the couplings is substantially the same for each of the appliances, and at least one of the appliances has a stiffness that is greater than the stiffness of at least one other appliance.

The present invention is also directed in another aspect toward a system for moving teeth of a patient's dental arch from a first tooth arrangement to a second tooth arrangement. In this aspect, the system comprises a plurality of resilient appliances, and each appliance has a row of spaced apart couplings for connection to respective teeth of the dental arch. The row of couplings of each appliance extends substantially along an arch-shaped curve that is substantially the same for each of the appliances when the appliances are relaxed. At least one appliance has a stiffness that is greater than the stiffness of at least one other appliance.

The present invention in another aspect is also directed toward a system for moving teeth of a patient's dental arch from a first tooth arrangement to a second tooth arrangement. In this aspect, the system comprises a plurality of resilient trays, and each tray has a row of receptacles for receiving respective teeth of the dental arch. Each of the receptacles of each tray is arranged in a certain relative orientation with respect to the remaining receptacles of the same tray when the tray is relaxed. The relative orientation of the receptacles is substantially the same for each of the trays. At least one of the trays has a stiffness that is greater than the stiffness of at least one other tray.

Another aspect of the present invention is also directed toward a system for moving teeth of a patient's dental arch from a first tooth arrangement to a second tooth arrangement. In this aspect, the system comprises a plurality of resilient trays, and each tray has a row of receptacles for receiving respective teeth of the dental arch. The row of receptacles of each tray when the tray is relaxed extends substantially along an arch-shaped curve that is substantially the same for each of the trays. At least one tray has a stiffness that is greater than the stiffness of at least one other tray.

The present invention is also directed in another aspect to a system for moving teeth of a patient's dental arch from a first tooth arrangement to a second tooth arrangement. In this aspect, the system comprises a plurality of resilient trays, and each tray has a row of receptacles defined by wall sections for receiving respective teeth of the dental arch. Each of the receptacles of each tray is arranged in a certain relative orientation with respect to the remaining receptacles of the same tray when the tray is relaxed. The relative orientation of the receptacles is substantially the same for each of the trays. The wall sections of at least one of the trays are constructed to provide a greater force per unit displacement against at least some of the teeth for a given dental arch configuration relative to the wall sections of at least one other tray.

In addition, the present invention is directed in another aspect to a system for moving teeth of a patient's dental arch from a first tooth arrangement to a second tooth arrangement. The system comprises a plurality of resilient trays, and each tray is identical in appearance. At least one of the trays has a stiffness that is greater than the stiffness of at least one other tray.

Optionally, all of the appliances (such as the trays) can be constructed using standardized or ideal arch forms. Moreover, the couplings of the appliances (such as the tooth receptacles of the trays) may have a configuration adapted to receive teeth within a selected range of sizes. Accordingly, the time and expense of designing and constructing custom-made appliances for each patient can be avoided.

These and other features of the invention are described in more detail in the paragraphs that follow and are illustrated in the accompanying drawings.

BRIEF DESCRIPTION OF THE DRAWINGS

FIG. 7 is a front elevational view of one resilient appliance of an orthodontic system according to still another embodiment of the invention, showing the appliance coupled to a row of connector members that are affixed to respective teeth of an exemplary dental arch of an orthodontic patient;

FIG. 8 is a view somewhat similar to FIG. 7 except that the appliance has been removed;

FIG. 9 is an enlarged side elevational view of one of the connector members alone that is shown in FIGS. 7 and 8;

FIG. 10 is an enlarged side cross-sectional view of the appliance and one of the connector members depicted in FIG. 7, along with the adjacent tooth;

DEFINITIONS

Figure 1:
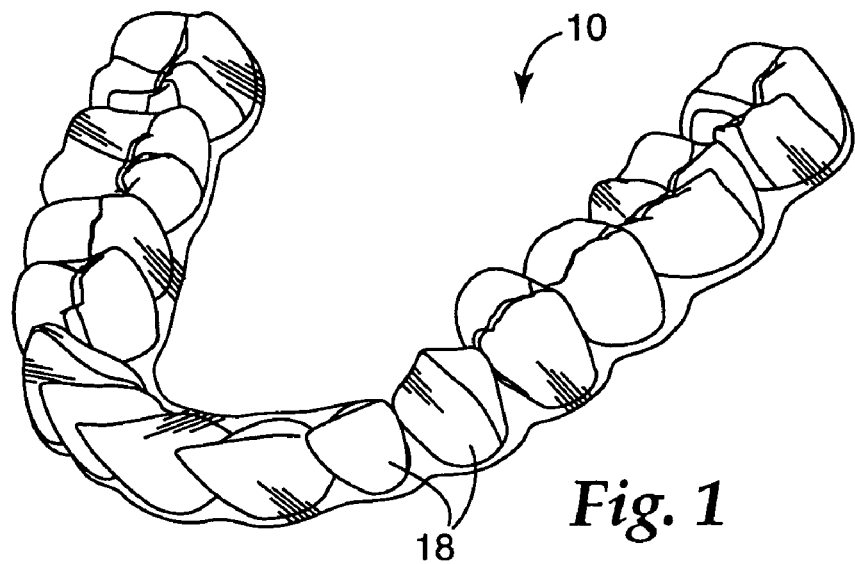
FIG. 1 is an inverted perspective view of one resilient appliance of an orthodontic system according to one embodiment of the present invention.

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Buccolabial" means in a direction toward the patient's cheeks or lips.

"Lingual" means in a direction toward the patient's tongue.

DETAILED DESCRIPTION OF THE PREFERRED EMBODIMENTS

A system for moving teeth of a patient's dental arch from a first tooth arrangement to a second tooth arrangement comprises a plurality of resilient appliances that are used in sequence. In the embodiment illustrated in FIGS. 1-3, the appliances comprise trays, and an exemplary tray of the system is broadly designated by the numeral 10. In FIGS. 2 and 3, the tray 10 is shown in use, placed over an exemplary dental arch 12 of an orthodontic patient. The tray 10 is shown alone in FIG. 1.

The tray 10 includes a row of spaced apart couplings or receptacles 14 (see FIG. 3), each of which is adapted to connect to and receive a respective tooth 16 of the patient's dental arch. The receptacles 14 are spaced apart from each other along the length of the tray 10, although adjoining regions of adjacent receptacles 14 are in communication with each other.

Each of the receptacles 14 includes at least one wall section 18 that is constructed to urge the respective tooth toward a desired orientation. In this embodiment, the wall sections 18 include a buccolabial wall section that extends across and contacts a buccolabial side of the tooth 16, a lingual wall section that extends across and contacts a lingual side of the tooth 16 and an occlusal wall section that extends across and contacts an occlusal portion of the tooth 16, preferably including the outermost occlusal edge of the tooth 16.

Figure 2:
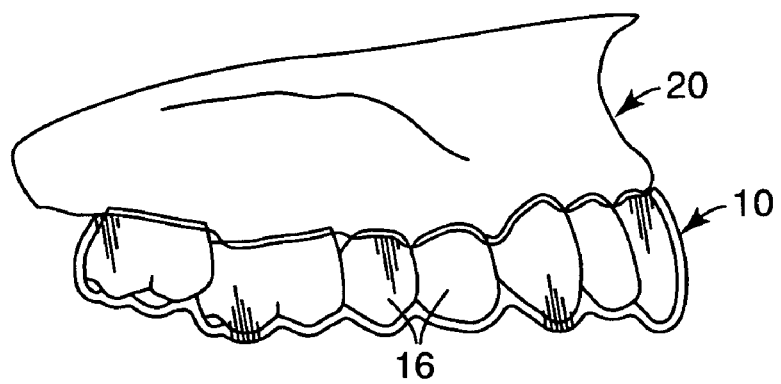
FIG. 2 is a side elevational view of the appliance and the dental arch shown in FIG. 1 illustrating the appliance in place over an exemplary dental arch of an orthodontic patient.
Figure 3:
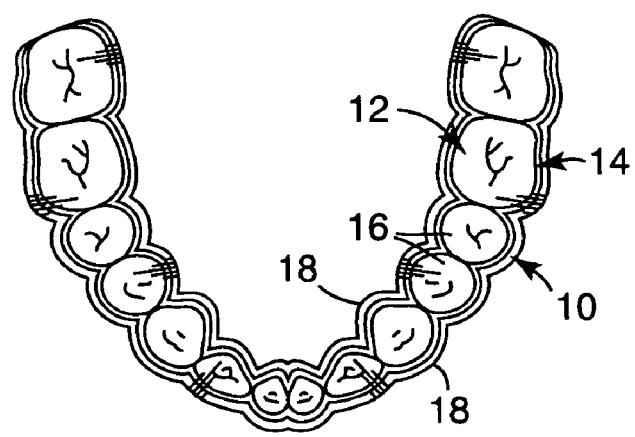
FIG. 3 is a bottom view of the appliance and the dental arch illustrated in FIG. 2.

In the embodiment of FIGS. 1–3, the inner surfaces of the buccolabial wall section, the lingual wall section and the occlusal wall sections matingly contact and are closely identical in shape to the buccolabial side, the lingual side and the occlusal portion respectively of the teeth 16. The gaps between the wall sections and the adjacent sides of teeth are shown in FIG. 3 only for purposes of illustration, and preferably are avoided so that the wall sections 18 are in close, complemental contact with the external tooth surfaces.

Each of the receptacles 14 for at least two of the trays of the series, more preferably for at least three trays of the series, and most preferably for all of the trays of the series is positioned in a desired orientation that matches the desired final orientation of the respective tooth at the conclusion of treatment. For example, in designing the tray 10, each tooth 16 has six degrees of freedom of movement. First, each tooth will have a desired angulation at the conclusion of treatment. Angulation may be defined according to the teachings of Dr. Lawrence A. Andrews as the mesiodistal cant of the facial axis of the clinical crown ("FACC") relative to a line perpendicular to the occlusal plane (see, e.g., *Straight Wire, The Concept and Appliance*, by Lawrence F. Andrews (L.A. Wells Co., copyright 1989)). Second, each tooth will also have a desired torque at the conclusion of treatment, and torque may be defined as the buccolabial-lingual cant of the FACC when measured from a line perpendicular to the occlusal plane. Third, each tooth 16 will have a desired rotation at the conclusion of treatment, and rotation can be defined as the rotational position of the tooth 16 in an arc about its long axis. Finally, each tooth 16 may be moved in translation in directions along three reference axes: a mesial-distal reference axis, a buccolabial-lingual reference axis, and an occlusal-gingival reference axis.

Optionally, the angulation, torque and crown prominence (i.e. the distance in a buccolabial direction from the embrasure line to each crown's most prominent facial point) of the teeth are identical to the known preferred values. Examples of suitable preferred values include those values associated with the treatment philosophies of Dr. Andrews or of Drs. McLaughlin, Bennett and Trevisi (such as embodied in the "MBT" brand brackets and buccal tubes from 3M Unitek Corporation) as set out in Tables I and II below. Additional information regarding the treatment philosophies of Drs. McLaughlin, Bennett and Trevisi is set out in their book entitled "Systemized Orthodontic Treatment Mechanics" (Mosby, 2001).

wall sections 18 may include an occlusal wall section for contact with the occlusal portion of the patient's tooth, but lack a buccolabial or a lingual wall section that is in contact with a majority of the buccolabial or lingual sides of the tooth 16. However, the wall sections 18 have sufficient area in contact with the tooth 16 to urge the tooth 16 toward its desired orientation.

Preferably, the receptacles 14 are arranged along a row when the tray 10 is relaxed that extends along a predefined arch-shaped reference curve such as an ideal embrasure line. An example of an embrasure line is designated by the letter "e" in FIG. 4 for the exemplary dental arch 12. The embrasure line is an imaginary curve, located at the level of the tooth crown's midtransverse plane that connects the most facial portions of the contact areas of all of the tooth crowns in the arch 12 when the teeth 16 are in desired orientations. A variety of embrasure lines are possible, including embrasure lines that extend along paths offset and

TABLE I

Maxillary Arch

|  | Central | Lateral | Cuspid | $1^{st}$ Bicuspid | $2^{nd}$ Bicuspid | $1^{st}$ Molar | $2^{nd}$ Molar |
| --- | --- | --- | --- | --- | --- | --- | --- |
| Andrews Crown Prominence, mm | 2.1 | 1.65 | 2.5 | 2.4 | 2.5 | 2.9 | 2.9 |
| Andrews torque, degrees | 7 | 3 | −7 | −7 | −7 | −9 | −9 |
| Andrews angulation, degrees | 5 | 9 | 11 | 2 | 2 | 5 | 5 |
| MBT torque, degrees | 17 | 10 | −7, +7 or 0 | −7 | −7 | −14 | −14 |
| MBT angulation, degrees | 4 | 8 | 8 | 0 | 0 | 0 | 0 |

TABLE II

Mandibular Arch

|  | Central | Lateral | Cuspid | $1^{st}$ Bicuspid | $2^{nd}$ Bicuspid | $1^{st}$ Molar | $2^{nd}$ Molar |
| --- | --- | --- | --- | --- | --- | --- | --- |
| Andrews Crown Prominence, mm | 1.2 | 1.2 | 1.9 | 2.35 | 2.35 | 2.5 | 2.5 |
| Andrews torque, degrees | −1 | −1 | −11 | −17 | −22 | −30 | −35 |
| Andrews angulation, degrees | 2 | 2 | 5 | 2 | 2 | 2 | 2 |
| MBT torque, degrees | −6 | −6 | −6, +6 or 0 | −12 | −17 | −20 | −10 |
| MBT angulation, degrees | 0 | 0 | 3 | 2 | 2 | 0 | 0 |

When the tray 10 is relaxed, the geometric orientation of each of the receptacles 14 matches the desired orientation of the respective tooth 16 at the conclusion of treatment. As a consequence, each of the receptacles 14 when the tray 10 is relaxed has a geometry sufficient to hold the respective tooth 16 in its desired final orientation with desired angulation, torque, rotation, and translation values, assuming that the tooth is free to move in space and is not constrained by other factors such as restraints imposed by the periodontal ligament and/or alveolar bone.

Optionally, the receptacle 14 does not have a shape that entirely matches the shape of the exposed portions of the tooth 16. For example, the wall sections 18 may be complemental to and contact the buccolabial and lingual sides of the tooth 16, but may not include an occlusal section in contact with the occlusal edge of the tooth 16. As another option, the parallel to the shapes of commonly available orthodontic archwires. Examples of suitable archwire shapes include the shapes of "OrthoForm I Tapered" brand archwires, "OrthoForm II Square" brand archwires and "OrthoForm III Ovoid" brand archwires from 3M Unitek Corporation. The receptacles are deemed to extend along the embrasure line when a negative image of the receptacles appears as an image of the teeth when in desired orientations along the embrasure line.

In the embodiment illustrated in FIGS. 1–3, the outer wall surfaces of the tray 10 including the outer surfaces of its buccolabial, occlusal and lingual wall sections are somewhat similar in shape to the underlying buccolabial, occlusal and lingual surfaces of the dental arch 12. This construction is an advantage, in that the volume occupied by the tray 10 in the oral cavity is reduced. However, other constructions are also possible. For example, the outer surfaces of the buccolabial and lingual wall sections 18 could extend along respective curves that follow in parallel to the embrasure line and lack recessed areas corresponding to the underlying interproximal regions of the dental arch 12.

In accordance with the present invention, a system for moving teeth of a patient's dental arch from a first tooth arrangement to a second tooth arrangement comprises two or more resilient appliances, and preferably at least three resilient appliances, such as the trays 10. The trays 10 are used in a pre-determined sequence in accordance with the progress of movement of the teeth from the first tooth arrangement to the second tooth arrangement.

Each tooth arrangement is an arrangement of the teeth at some point in time during the course of treatment. As described herein, for example, the first and second arrangements could be the initial and final arrangements respectively. Alternatively, the first and second arrangements could be the initial and next subsequent arrangements respectively, or the next-to-final and final arrangements respectively. As another alternative, the first and second arrangements could both be arrangements at intermediate points during the course of treatment.

Figure 4:
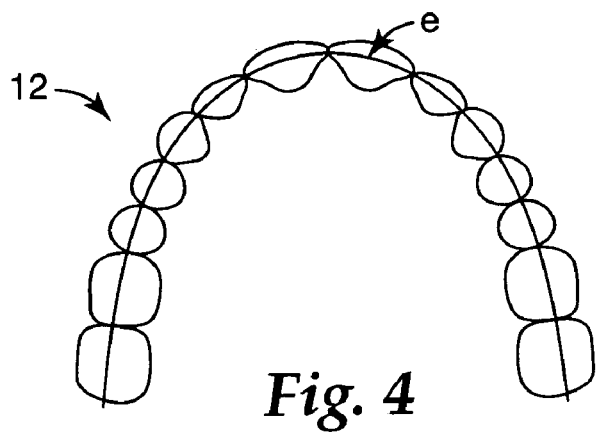
FIG. 4 is a bottom view of an exemplary ideal dental archform, illustrating the location of an embrasure line.

In one embodiment of the invention, at least two trays of the series, more preferably at least three trays of the series and most preferably all of the trays of the series are identical in appearance when relaxed. Consequently, in this embodiment, the row of receptacles of each tray when the tray is relaxed extends along the same embrasure line, such as the embrasure line "e" that is depicted in FIG. 4.

Furthermore, the relative orientation of the receptacles with respect to the remaining receptacles of the same tray when the tray is relaxed is substantially the same for each of the trays, and is preferably identical for each of the trays. For example, the orientation of a receptacle may be determined by reference to a hypothetical axis that is collinear with the FACC of the tooth when the tooth is received in the receptacle. In this example, for instance, the spacing and angular orientation between this hypothetical axis of the receptacle for the upper right lateral tooth and the hypothetical axis of the receptacle for the upper right cuspid tooth are the same for each tray of the system when the trays are relaxed. Similarly, the spacing and angular orientation between other receptacles are the same for each tray of the system when the trays are relaxed.

However, at least one of the trays of the series and preferably at least two trays of the series are constructed to provide a greater force against at least some of the teeth for a given dental arch relative to the force provided against the same teeth by at least one other tray of the system. For example, at least one tray has a stiffness that is greater than the stiffness of at least one other tray. The stiffness may be varied among the trays by altering the composition or processing conditions of the material used to make the trays, by changing the construction of the trays (for example, by changing the thickness of the wall sections 18 in a buccolabial-lingual direction), or by other methods. The stiffness may be determined by any suitable method, such as the tensile strength test that is set out in ASTM Test Method D412 for elastomeric materials or the tensile strength test that is set out in ASTM Test Method D882 for plastic materials.

Preferably, each tray of the series has a different stiffness, and the trays are selected so that the stiffness increases as treatment progresses. For example, the series may include at least three trays, each having a greater stiffness than the previous tray when used in the proper sequence. In this manner, the trays used in the earlier stages of treatment, such as the initial tray, provide a relatively light force per unit displacement on the teeth.

As treatment progresses and as the teeth are moved closer to a desired tooth arrangement, stiffer trays are utilized. The increased stiffness of subsequent trays of the system provides additional force on the teeth to help ensure that the teeth are moved to their final desired positions, even though the amount of remaining necessary tooth movement is relatively small. The increased stiffness also helps to stabilize the teeth and hold the teeth firmly in place without undue movement while the teeth are in or near desired final positions. Additionally, the increased stiffness of subsequent trays of the system helps ensure that there is sufficient force to overcome the minimum, threshold force necessary to continue movement of the teeth to final positions.

Optionally, all of the trays of the series are made in advance by a manufacturer according to a set of statistical averages or norms. For example, data could be gathered from a number of individuals regarding the size of each tooth, including the thickness of the tooth in a buccolabial-lingual direction, the height of a tooth in an occlusal-gingival direction and the width of a tooth in a mesial-distal direction. Optionally, the thickness of the tooth is the greatest buccolabial-lingual thickness taken in a reference plane that passes through the facial axis point. The height of the tooth, or cusp height, is measured from the cusp tip to the depth of the central sulcus midway mesiodistally. The width of the tooth is determined by measuring the greatest mesio-distal diameter of the tooth.

Next, a number of possible size ranges is developed using statistical analysis in order to determine the optimal configuration of each of the receptacles for the trays of each series. For example, five series of trays can be developed corresponding to five different ranges of overall arch length as determined along a curved mesial-distal reference axis. Each series includes trays with receptacles adapted to fit a range of sizes so that, in all likelihood, one tray series and possibly two will include trays having receptacles adapted to receive the teeth of any particular patient with a relatively close mating fit.

For instance, the gathered tooth data could be analyzed for each tooth such that the mean tooth height and mean tooth thickness are derived for receptacles adapted to fit a certain range of tooth widths. The dimensions of the receptacles that correspond to the tooth heights and tooth thicknesses are then selected to receive the respective teeth in relatively close complemental relationship for each chosen range of tooth widths. The analysis is repeated for each receptacle of each series. Generally speaking, the mean tooth height and mean tooth thickness are known to increase and decrease in proportion to the increase and decrease in tooth width. Consequently, the practitioner can select the proper series for a best fit from a choice of different, pre-manufactured series based only on a determination of the tooth widths of some or all of the teeth of the patient in need of treatment.

The manufacture and supply of two or more series of trays in advance of knowing individual patient data (such as the patient's tooth sizes or type of malocclusion) is a significant advantage, in that the manufacturer and/or practitioner can maintain an inventory of trays in advance. Once the practitioner has selected a series of trays that best fit the patient at hand, the first tray of the series can be retrieved from inventory for the prompt initiation of treatment. Moreover, the need to make additional trays once treatment is underway can be avoided, such as in instances in the past where custom-made trays have not moved the teeth as intended and a mid-course correction with another custom tray is needed.

Selection of the proper series of trays for any particular patient can be carried out by any one of a number of methods. For example, the practitioner may use manual methods such as calipers to determine the height, width and/or thickness of each tooth. The practitioner can then consult manufacturer's data regarding the various available series of trays, so that the series providing the best fit can be chosen.

Alternatively, the practitioner may obtain a digital data file regarding the tooth shapes of the patient. The data file may be obtained by an intra-oral scanner, or by a scanner that scans either an impression of the patient's teeth or a model of the patient's teeth. The data file may include data regarding the height, width, thickness, or volume of each tooth, or any combination of the foregoing. Optionally, this data file may also include information regarding the shape and/or orientation of each tooth. Computer software can then be employed to analyze the data and select a particular series of trays from a number of different series.

For example, the software can select the best series by analyzing the data regarding tooth widths, and then selecting the series by comparing the widths of the receptacles of various series to the corresponding widths of the teeth. As another example, the software can select the best series by first determining the desired tooth positions at the conclusion of treatment, and then fitting a hypothetical curve to the embrasure line of the teeth at the conclusion of treatment. This embrasure line is then compared to the arch-shaped curve along which the receptacles of the various series extend, in order to select the series that presents a curve that most closely matches the desired embrasure line at the conclusion of treatment. Optionally, the embrasure line used by the software for purposes of comparison may extend along all of the teeth of the patient's dental arch, or along only a portion of the patient's dental arch.

Optionally, the manufacturer may assist the practitioner in the selection of the best series of trays. For instance, the practitioner may transmit the tooth data to the manufacturer via the Internet so that the manufacturer can use the software mentioned above and, with the practitioner's approval, promptly ship the selected series to the practitioner, preferably from an inventory of previously manufactured trays. As another alternative, the practitioner can use the software mentioned above in the practitioner's office or via an interactive program connected by the Internet to the manufacturer's facilities, and pick the best series from an inventory maintained in the practitioner's office.

Optionally, the height of one or more of the receptacles in an occlusal-gingival direction may be greater than needed to receive the patient's tooth at the beginning of use of the tray. Such construction facilitates the continued eruption of teeth that have only partially erupted and helps ensure that the tray does not hinder the tooth in reaching its full desired height at maturity. In this example, data for a particular patient regarding the height of some of the patient's teeth may be ignored for the purpose of selecting the best series of trays.

As an additional option, the first tray of the series may have receptacles with additional space adjacent its buccolabial wall section or lingual wall section. This additional space is an advantage in instances where the patient's teeth are significantly crowded at the beginning of treatment.

Preferably, the trays including the tray 10 are comprised of an aesthetically pleasing material that is resistant to staining by food and beverages. Preferably, the material is colorless, and preferably transmits light in the visible wavelengths. Preferably, the material transmits sufficient light so that the natural color of the patient's tooth can be observed through the tray.

The trays are preferably made of resilient polymeric materials such as polyurethane, silicone, latex, fluoropolymer and polyolefin. Examples of suitable polyurethane materials include polyester-based materials (such as Texin 285 brand, Texin 390 brand and Desmopan 453 materials, all from Bayer). Other suitable polyurethane materials include Pellethane brand polytetramethylene glycol ether nos. 2363-80A, 2363-55D and 2363-62D, all from Dow Chemical. Other suitable polyurethane materials include Tecoflex brand polyether-based material, nos. 80A, 60D and 72D, all from Themedics.

Suitable silicone materials for the tray include RD 10333 brand silicone from RD Rubber, MED-4725 and MED-4755 brand silicone from NuSil, no. 50069 silicone from Rhodia Silicones, LIM6071 silicone from General Electric and Baysilone brand silicone, no. LSR 2670 from Bayer. Suitable rubber materials include K-100 natural rubber and K-3800 thermoplastic rubber from Kent Elastomer. Suitable fluoropolymer materials include no. FC 2145 fluoroelastomer from 3M Dyneon.

The trays may comprise a viscoelastic material. As an option, the viscoelastic material can be manually deformed to a permanent or semipermanent change in configuration by the practitioner so that, for example, a particular receptacle can be extended in a direction to better accommodate a severely malpositioned tooth. Preferably, the viscoelastic material has sufficient inherent memory to urge the receptacle back toward its original position over a period of time. Preferably, the viscoelastic material exhibits a tan δ in the range of about 0.01 to about 2.0, where tan δ is defined as the ratio of the shear loss modulus (G") to the shear storage modulus (G') as described, for example, in *Viscoelastic Properties of Polymers*, by John D. Ferry (third edition, John Wiley and Sons, Inc., copyright 1980).

Optionally, the series of appliances may include other appliances as well. For example, the series may include two or more identical trays with the same stiffness. Identical trays may be desired in instances where the tray is replaced with an identical tray after a length of time, such as in instances where the tray is subject to undue wear or in instances where the stiffness of the tray significantly changes over a period of time. The series of appliances may also include other types of appliances, such as a brace comprising brackets and an archwire for use in the final stage of treatment and after use of the trays has been concluded.

Figure 5:
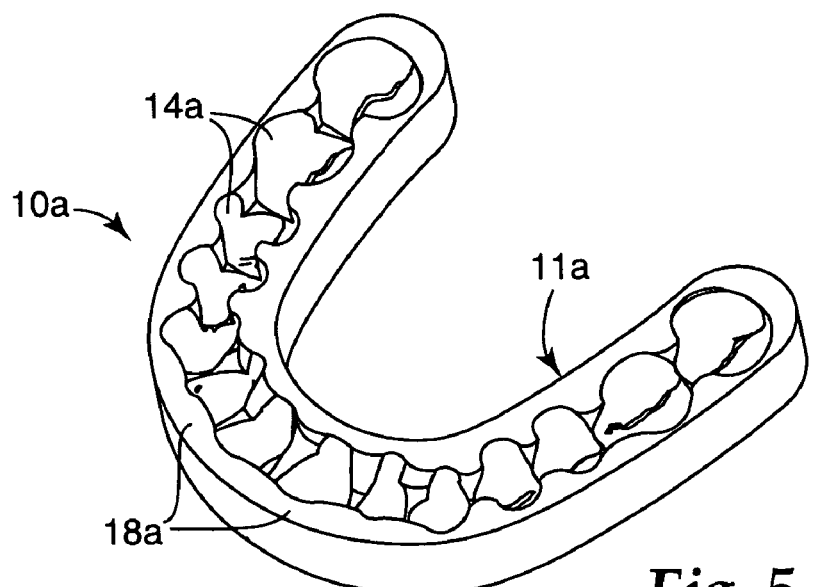
FIG. 5 is a perspective view of one resilient appliance of an orthodontic system according to another embodiment of the invention.

A system for moving teeth of a patient's dental arch according to another embodiment of the invention also comprises a series of trays, one of which is designated by the numeral 10a in FIG. 5. The tray 10a includes a row of spaced apart couplings or receptacles 14a, each of which is adapted to receive and connect to a respective tooth of a patient's dental arch.

The tray 10a is somewhat similar to the tray 10, except that the tray 10a has wall sections 18a that present a smoothly curved buccolabial surface and a smoothly curved lingual surface. The buccolabial and lingual surfaces in this embodiment extend in parallel relationship to an embrasure line (not shown in FIG. 5). Such construction provides regions of increased wall section thickness, particularly in regions adjacent the underlying interproximal areas of the patient's dental arch. In other aspects, the tray 10a is essentially the same as the tray 10 described above.

Figure 6:
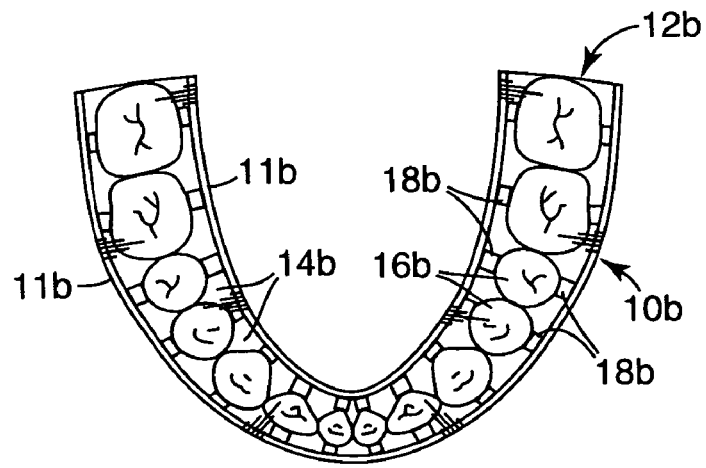
FIG. 6 is a view somewhat similar to FIG. 3 except showing one resilient appliance of an orthodontic system according to yet another embodiment of the invention.

A system for moving teeth of a patient's dental arch according to another embodiment of the invention comprises a series of trays that is exemplified by the tray 10*b* shown in FIG. 6. The tray 10*b* includes a shell-like frame 11*b* having an overall, generally "U"-shaped configuration that is adapted to fit over the dental arch of an orthodontic patient. The frame 11*b* also has a generally "U"-shaped configuration in cross-sections taken in reference planes perpendicular to the curved central axis of the frame 11*b*.

The tray 10*b* includes a series of spaced apart wall sections 18*b* that are fixed to the frame 11*b*. Some of the wall sections 18*b* extend in a lingual direction from the buccolabial side of the frame 11*b*, while the remaining wall sections 18*b* extend in a buccolabial direction from the lingual side of the frame 11*b*. Each pair of opposed wall sections 18*b* partially defines a receptacle 14*b* for receiving a tooth 16*b* of a dental arch 12*b*.

Optionally, the protruding wall sections 18*b* are made of a material that is different from the material of the frame 11*b*. For example, the wall sections 18*b* may be made of a material that has less stiffness or greater stiffness than the stiffness of the material of the frame 11*b*. The wall sections 18*b* may also be provided with surface structure such as a roughened surface that facilitates firm, essentially non-sliding contact between the wall sections 18*b* and the engaged surfaces of the tooth 16*b*.

Preferably, the frame 11*b* is made of a material that deforms when the tray 10*b* is placed over the maloccluded teeth. The inherent resiliency of the frame 11*b* then tends to move the teeth toward desired positions. When the tray 10 is relaxed, the buccolabial and lingual sides of frame 11*b* preferably follow in parallel along respective curves that are parallel to the desired reference curve such as the embrasure line. As such, the configuration of the frame 11*b* when the tray is relaxed will match the configuration of the frame 11*a* once the teeth of the dental arch 12*b* have moved to their desired positions.

Except as described above, the series of trays that includes the tray 10*b* is essentially the same as the series of trays that includes the tray 10 set out above. For example, in one embodiment at least one tray of the series of trays that includes the tray 10*b* that is having a stiffness that is greater than the stiffness of at least one other tray of the same series. The variation in stiffness may be carried out by modifying that material of the wall sections 18*b*, by modifying the material of the frame 11*b*, by varying the thickness of the wall sections 18*b* and/or of the frame 11*b*, or by any combination of the foregoing. Moreover, at least two trays of the series that includes the tray 10*b* includes a row of the receptacles that extends along substantially the same arch-shaped reference curve such as the embrasure line, and the receptacles are arranged in a certain relative orientation with respect to remaining receptacles of the same tray when the tray is relaxed.

A system for moving teeth of a patient's dental arch from a first tooth arrangement to a second tooth arrangement according to another embodiment of the invention is depicted in FIGS. 7–10 and comprises a plurality of resilient appliances or arch members 22 used in sequence. An exemplary arch member 22 is shown in FIGS. 7 and 10. The arch member 22 along with a series of connector members 24 together comprise an orthodontic brace that is broadly designated by the numeral 20.

Each of the connector members 24 is affixed to a respective tooth 26 of a patient's dental arch 28. In FIGS. 7, 8 and 10, the illustrated dental arch 28 is an exemplary maxillary or upper dental arch, although it should be understood in this regard that the brace 20 may be adapted for use with the mandibular or lower dental arch as well.

FIG. 8 is an illustration somewhat similar to FIG. 7, except that the arch member 22 has been removed. As shown, the connector members 24 are directly bonded to the enamel surface of the patient's teeth 26. Preferably, each tooth 26 of the dental arch 28 receives a connector member 24, although alternative arrangements are also possible. For example, the connector members 24 may be attached to all of the teeth 26 in the dental arch 28 except for the molar teeth, or may be attached to only certain selected teeth as may be desired by the practitioner.

FIG. 9 is a side elevational view of the connector member 24 alone. The connector member 24 includes a base 30 having an external surface that is adapted to be directly bonded to the enamel surface of the patient's tooth 26 by an adhesive. Optionally, the external surface of the base 30 has a compound concave contour that precisely matches the convex compound contour of a particular tooth. Optionally, the base 30 is provided with means for enhancing the bond between the connector member 24 and the selected adhesive, such as a roughened or dimpled surface, a surface having particles (irregularly-shaped or regularly-shaped) fixed to the base 30, structure for providing a mechanical interlock with the adhesive when hardened, chemical bond-enhancing means or any combination of the foregoing.

The connector member 24 includes a body 32 that is connected to the base 30. The body 32 has a neck portion 34 that presents an undercut region. The body 32 also includes a bulbous outer head 36 that is connected to the neck 34.

Preferably, the connector member 24 is made as a single, unitary component such that the body 32 is integrally connected to the base 30. Preferably, the connector member 24 is integrally made of an aesthetic material such as a material that is translucent or transparent to light in the visible wavelengths. As another option, the connector member 24 has a color that matches the color of the patient's adjacent dentition. If the connector member 24 is made of a transparent or translucent material, the material preferably transmits sufficient light to enable the color of the patient's underlying tooth to be visible through the front or labial side of the connector member 24.

Examples of suitable materials for constructing the connector member 24 include ceramic materials, such as single crystal alumina and polycrystalline alumina. Alternatively, the connector member 24 may be made of a polymeric material such as polycarbonate. Optionally, the polymeric material is reinforced with glass fibers. Suitable ceramic materials are described, for example, in U.S. Pat. Nos. 4,954,080 and 6,648,638. Suitable polymeric materials are described, for example, in U.S. Pat. No. 5,445,770.

The arch member 22 includes a row of couplings or receptacles 38, one of which is designated in FIG. 10. The receptacles 38 are spaced apart from each other along the length of the arch member 22. As depicted in FIG. 7, each of the receptacles 38 is an opening that receives the head 36 of a respective connector member 24. Each of the receptacles 38 has a configuration adapted to releasably receive the head 36 in snap-fit relation. Consequently, the arch member 22 can be disconnected from the connector members 24 when desired.

The exemplary receptacles 38 shown in FIG. 7 surround the head 36 of each connector member 24 along the buccolabial, occlusal, mesial, gingival and distal sides of each head 36. However, other constructions are also possible. For example, the receptacles 38 may extend completely through the arch member 22 such that the receptacles 38 comprise apertures and buccolabial sides of the heads 36 are exposed when viewing the brace 20 in a lingual direction.

The arch member 22 illustrated in FIG. 7 is shown in enlarged cross-sectional view in FIG. 10. In this embodiment, the arch member 22 is made of a single layer of polymeric material having sufficient resiliency to receive the connector members 24 in snap-fit relation. To this end, the polymeric material deforms to enlarge the opening of the receptacle 38 as the arch member 22 is urged in a lingual direction in order to receive the head 36 of the respective connector member 24.

The arch member 22 is preferably made of an aesthetically pleasing material such as translucent, transparent or tooth-colored polymeric materials. If the arch member 22 is made of a translucent or transparent material, the material preferably transmits sufficient light to enable the color of the patient's underlying dentition to be visible through the front or labial side of the arch member 22. Optionally, reinforcing fibers such as glass fibers can be embedded in the polymeric material of the arch member 22. Suitable materials for making the arch member 22 include the polymeric materials described above in connection with the tray 10.

Preferably, the arch member 22 is capable of changing from a first state that facilitates removal and/or installation of the arch member 22 to a second state that facilitates orthodontic treatment. The change in state may comprise, for example, a change in material property or a change in shape, and is preferably induced by an environmental change that can be carried out in the patient's oral cavity. The change in state may occur throughout the arch member 22 or only in selected portions of the arch member 22.

As one example, the arch member 22 may comprise a shape memory polymer such as "Calo-MER" from Polymer Technology Group, elastic memory composite ("EMC") from Composite Technology Development, Inc. or "Veriflex" from Cornerstone Research Group. These materials have both a high and a low temperature transition. For instance, the polymeric material may have a lower glass transition temperature that is in the range of about 23° C. to about 37° C., and more preferably in the range of about 25° C. to about 35° C., and a higher transition temperature that is in the range of about 40° C. to about 50° C. The arch member 22 is shaped to conform to a model of the patient's teeth in desired positions at a temperature above the higher transition temperature, and then held in that shape as it is cooled to a temperature below its higher transition temperature. Next, the arch member 22 is shaped to conform to a model of the patient's teeth in current conditions at a temperature that is between the high and low transition temperature, and held in that shape while it is cooled to a temperature below the lower transition temperature. Such construction facilitates the initial connection of the arch member 22 to the connector members 24, such as in instances where the initial connection is carried out before the arch member 22 approaches body temperature. If the lower transition temperature is between room temperature and body temperature, the material will undergo a change in state once the arch member 22 is placed in the oral cavity and will subsequently provide forces for moving the teeth toward desired positions.

As another example, the arch member 22 may be made of a material that has a glass transition temperature above body temperature, and is shaped to provide for easy installation or removal at temperatures above its glass transition temperature. In this example, the arch member 22 is kept at a temperature below its transition temperature before installation. When it is desired to remove the arch member 22, it is warmed to a temperature above its glass transition temperature.

Alternatively, the arch member 22 may be constructed of homopolymers, cross-linked homopolymers, copolymers, cross-linked copolymers, or blends thereof with inherent memory as described in U.S. Pat. No. 6,183,248. Optionally, the material may have only a single transition temperature. To form the memory removal mechanism, these materials may be formed into a strip that loosely approximates the shape of the arch. Once formed into this arch shape, the strip is shaped at a temperature above its transition temperature such that it will deliver desired forces to the teeth, held in that shape and then cooled to a temperature below its transition temperature. Once the strip is in the mouth, heating the strip above the glass transition temperature will loosen it from the appliances. The change in state may also be carried out by methods other than a temperature change. For instance, the polymeric material may change its state when subjected to an aqueous buffer solution having a predetermined pH ratio. Alternatively, the change in state may occur when the polymeric material absorbs liquid as a result of a change in ionic strength or upon exposure to radiation from a source of light. The change in state may be a change in shape such as expansion or shrinkage, and may also or in the alternative provide a change in material property such as rigidity (i.e. flexural rigidity) or durometer hardness.

The change in state may be selected to facilitate reception or disengagement of the heads 36 in the respective receptacles 38. For example, the change in state may provide an enlargement of the openings to the receptacles 38 when desired, so that less force is needed to insert the heads 36 in the receptacles. Once the insertion is complete, a reversal of the change in state contracts the openings in order to reduce the probability of unintentional detachment of the heads 36 from the arch member 22 during the course of treatment.

Other suitable polymeric materials that undergo a change in state are described in U.S. Pat. Nos. 6,183,248, 5,506,300 and 6,388,043, and U.S. Patent Application Publications Nos. U.S. 2003/0157454 and 2003/0055198.

The arch member 22 may also be made of a multi-component material comprising multiple layers. As one example, some of the layers or components could undergo a change in state (such as a glass transition) to reduce the modulus of the arch member 22 for facilitating installation or removal of the arch member 22, while other layers or components remain rigid to help maintain the shape of the arch member 22. For instance, one layer may have a transition temperature of about 150° C. while a second layer may have a transition temperature of about 40° C. Additionally, one or more of the layers could vary in thickness in different regions along the length of the arch member 22. Examples of suitable multi-component materials are described in the above-mentioned U.S. Pat. No. 6,183,248.

The materials described above for making the arch member 22 along with the methods of constructing the arch member 22 may be used as well for making trays according to other embodiments of the invention, including the tray 10.

Preferably, each arch member 22 of the series has a geometry identical to the geometry of at least one other, and preferably all of the arch members of the series. The geometry of the arch member 22 when relaxed corresponds to the geometry necessary to move the teeth to the desired final positions. When the arch member 22 is placed on the connector members 24, however, the geometry of the arch member 22 is changed to a temporary shape corresponding to the shape of the tooth arrangement prior to reaching the desired intermediate or final arrangement, such as the current tooth arrangement. The resilient properties of the polymeric material function to exert forces on the teeth 26 as necessary to shift the teeth to the desired intermediate or final arrangement.

As treatment progresses and as the teeth 26 move closer to their desired final positions, the arch member 22 is removed from the connector members 24 and replaced with another arch member from the same series. The second arch member has a stiffness that is greater than the stiffness of the first arch member and consequently provides greater force on the teeth per unit displacement than the force provided by the first arch member. The stiffness may be varied by any of the methods described above in connection with the trays 10, 10*a*, 10*b*.

Preferably, the arch member 22 is connected to the connector members 24 such that the arch member 22 may exert forces on the connector members 24 and hence on the underlying teeth 26 in a number of different directions. For example, the arch member 22 can preferably exert forces as may be needed to move the connector members 24 in either or both translation and rotation with respect to three mutually perpendicular reference axes. As a result, the teeth 26 may be subjected to tipping, torquing or angulation movements as desired. To this end, the heads 36 and the receptacles 38 preferably have matching polygonal shapes, matching key and keyway shapes or other interlocking configurations that facilitate transmitting the desired forces from the arch member 22 to the connector members 24 and ultimately to the underlying teeth.

In addition to the arch member 22, or as an alternative, the connector members 24 may be made of a material that changes from a first state to a second state, wherein the first state facilitates coupling or uncoupling of the connector members 24 from the arch member 22 and the second state facilitate orthodontic treatment. For example, the connector members 24 may be made of a shape memory material as described above, and contracts in shape when cooled in order to ease insertion of the heads of the connector members 24 into the receptacles 38.

Additional aspects of the brace 20, including alternative constructions of the arch member 22 and the connector members 24, are set out in applicant's pending U.S. patent application entitled "ORTHODONTIC BRACE WITH POLYMERIC ARCH MEMBER", Ser. No. 10/865,649 filed Jun. 10, 2004.

Figure 11:
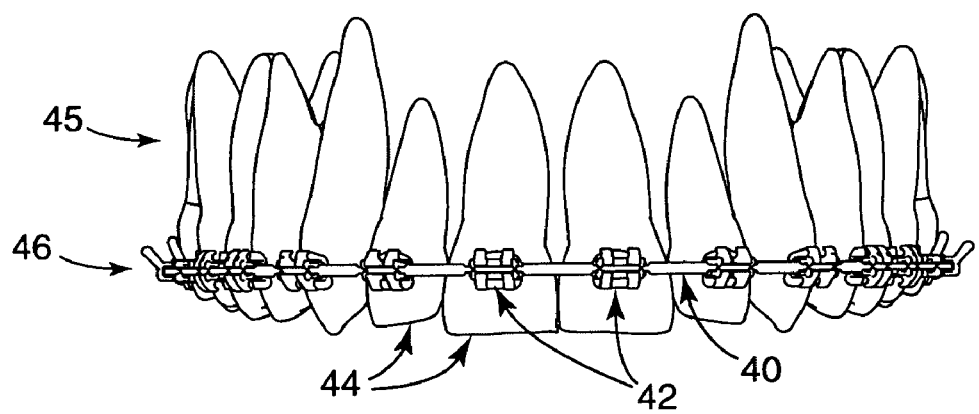
FIG. 11 is a front elevational view of one resilient appliance of an orthodontic system according to yet another embodiment of the invention, illustrating the appliance connected to a row of brackets that are affixed to teeth of an exemplary dental arch of an orthodontic patient.
Figure 12:
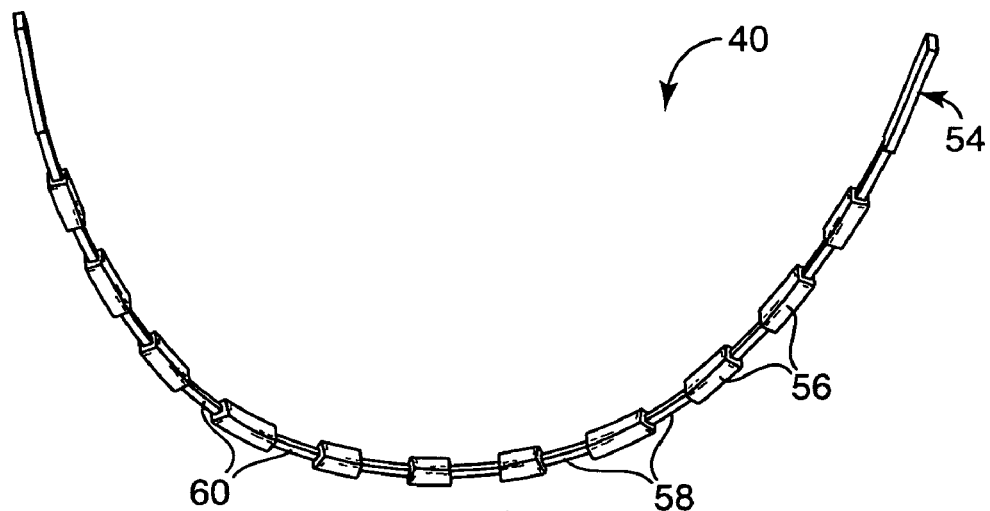
FIG. 12 is a perspective view of the appliance alone that is shown in FIG. 11.
Figure 13:
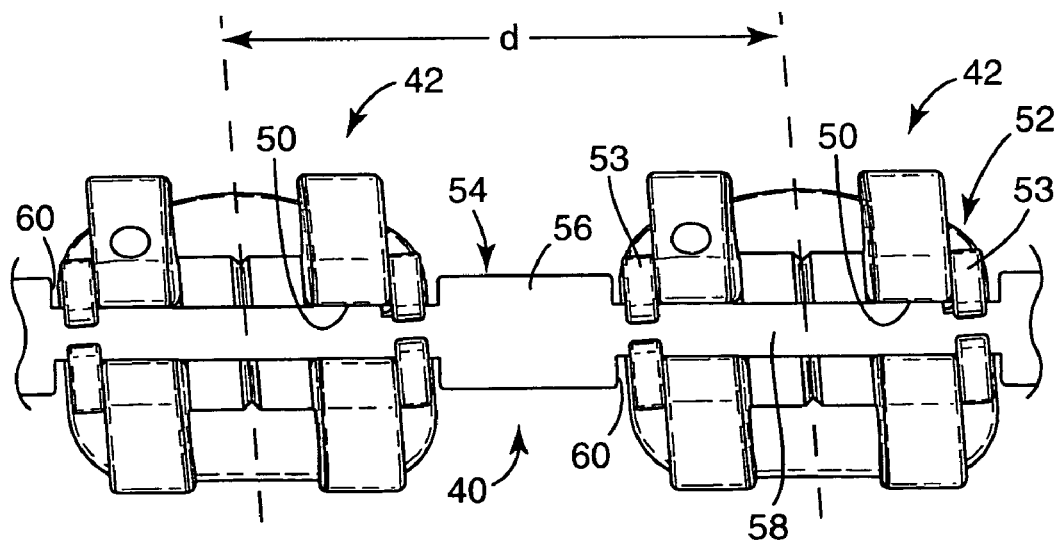
FIG. 13 is an enlarged, fragmentary, front elevational view of a portion of the resilient appliance along with two of the brackets that are illustrated in FIG. 11.

A system for moving teeth of a patient's dental arch from a first tooth arrangement to a second tooth arrangement according to still another embodiment of the invention comprises a plurality of resilient appliances or arch members, an exemplary one of which is the arch member 40 shown in FIGS. 11–13. In this embodiment, the arch member 40 is connected to a set of orthodontic brackets 42, each of which is fixed to a corresponding one of the patient's teeth 44. The arch member 40 in combination with the brackets 42 comprises an orthodontic brace that is broadly designated by the numeral 46.

Examples of suitable brackets 42 are illustrated in enlarged view in FIG. 13. The illustrated brackets 42 are known as a "self-ligating" brackets and are similar to the appliances described in U.S. Pat. Nos. 6,302,688 and 6,582,226. Each bracket 42 has an elongated archwire slot 50 that extends across the bracket 42 in a generally mesial-distal direction.

The exemplary self-ligating brackets 42 illustrated in FIGS. 11 and 13 have a latch 52 for releasably retaining an archwire or arch member (such as arch member 40) in the archwire slot 50. In this embodiment, the latch 52 comprises a pair of resilient clips 53 having a generally "C"-shaped configuration. Preferably, the clips 53 are sufficiently flexible to enable the practitioner to insert the arch member 40 in the archwire slot 50 by pressing the same in a lingual direction such that the sides of the clips 53 deflect outwardly and away from each other. Once the arch member 40 is clear of the outer arm portions of the clips 53 and is located in the archwire slot 50, the sides of the clips 53 self-deflect and spring back toward each other to their normal closed orientation in order to retain the arch member 40 in the archwire slot 50.

Preferably, the sides of the clips 53 deflect outwardly in enable the latch 52 to assume a slot-open orientation and release the arch member 40 from the archwire slot 50 whenever the force exerted by the arch member 40 on the bracket 42 exceeds a certain minimum value. This minimum value is sufficiently high to prevent the arch member 40 from unintentionally releasing from the archwire slot 50 during the normal course of orthodontic treatment. As such, the arch member 40 can exert forces on the bracket 42 sufficient to carry out the intended treatment program and move the associated tooth as desired. Further details and additional options for the brackets 42 are set out in the aforementioned U.S. Pat. Nos. 6,302,688 and 6,582,226.

Other types of self-ligating brackets are also possible. For example, the bracket 42 may be identical or similar to the self-ligating appliances described or referenced in U.S. Pat. Nos. 4,248,588, 4,492,573, 4,712,999 and 5,711,666.

As another alternative, the bracket 50 need not be a self-ligating bracket. For example, the bracket may lack a latch and be provided with two or more projections known as "tiewings" that are located on opposite sides of the archwire slot. In practice, the arch member 40 is retained in the archwire slot of such a bracket by extending a ligature around the tiewings as well as over the arch member 40 in order to retain the latter in the archwire slot. Suitable ligatures include tiny, elastomeric O-ring ligatures as well as sections of small-diameter metallic wire with ends that are twisted together to form a loop. As yet other options, the brackets may be replaced by buccal tubes or any other type of tooth-connecting member that has a passage or slot for receiving the arch member 40.

The arch member 40 is shown alone in FIG. 12. The arch member 40 includes an elongated body 54 that is made of a resilient material and has an overall, generally "U"-shaped configuration in plan view. Optionally, the body 54 when relaxed extends along a reference plane that is parallel to the desired occlusal plane of the patient.

As depicted in FIG. 12, the body 54 includes a series of enlarged sections 56 that are connected together by narrowed sections 58. As shown, the cross-sectional area of the enlarged section 56 is larger than the cross-sectional area of the narrowed section 58. Such construction presents a series of couplings or notches 60 that are spaced along the length of the body 54. Each notch 60 extends inwardly from an outer edge of the arch member 40 in a direction toward the curved, central longitudinal axis of the arch member 40.

In the illustrated embodiment, the notches 60 are located along an occlusal edge (i.e., an edge facing the outer tips of the patient's teeth) of the arch member 40 as well as along a gingival edge (i.e., an edge facing the gums or gingiva of the patient) of the arch member 40. However, other constructions are also possible. For example, the narrowed sections 58 could be located along the occlusal edge of the arch member 40 such that the notches 60 are only present along the gingival edge of the arch member 40.

In this embodiment, the enlarged sections 56 as well as the narrowed sections 58 have a cross-sectional shape that is generally rectangular with rounded corners. However, other constructions are also possible. For example, the cross-sectional shapes of the sections 56, 58 may be elliptical, oval or circular. Combinations of such shapes are also possible. For example, the enlarged sections 56 may have an oval shape in cross-section, while the narrowed sections 58 may have a generally rectangular configuration in cross-section. As used herein with reference to the arch member 40, the term "cross-section" means a cross-section that is generally perpendicular to the curved, central longitudinal axis of the arch member 40.

The narrowed sections 58 are received within the archwire slots 50 of the bracket 42. To this end, and in this embodiment, the narrowed sections 58 have an overall size or height in an occlusal-gingival direction that is less than the occlusal-gingival size or height of the archwire slot 50. The narrowed sections 58 also have an overall thickness in a buccolabial-lingual direction that is less than the distance between the bottom or lingual side of the archwire slot 50 and the outer arm portions of the clip 53 so that the clip 53 may close to retain the arch member 40 once the narrowed section 58 is received in the archwire slot 50.

Preferably, the cross-sectional configuration of the narrowed section 58 is complemental to the cross-sectional configuration of the archwire slot 50. For example, the archwire slot 50 has a rectangular shape, and the narrowed section 58 has a matching rectangular shape that is just slightly smaller, such as 0.001 inch or 0.025 mm in height and width. As a result, the narrowed section 58 substantially fills the archwire slot 50 and provides good control over movement of the associated tooth without undue tolerance or "slop".

The body 54 has a major cross-sectional axis and a minor cross-sectional axis when considered in reference planes perpendicular to the longitudinal axis of the body 54 and between adjacent notches 60. For example, the enlarged section 56 of the body 54 has a major cross-sectional axis that extends in a generally vertical direction viewing FIG. 13, and a minor cross-sectional axis that extends in a generally horizontal direction viewing FIG. 13. Consequently, the body 54 adjacent the notch 60 (i.e., in areas next to the notch 60 in a occlusal-gingival direction) has an overall size or height in an occlusal-gingival direction that is less than the length of the major cross-sectional axis.

However, the enlarged section 56 of the body 54 need not necessarily have a major cross-sectional axis and a minor cross-sectional axis. Instead, the enlarged section 56 may have a vertical cross-sectional axis and a horizontal cross-sectional axis that are equal in length. For example, the cross-sectional shape of the enlarged section 56 may be square or circular.

In the embodiment illustrated in FIGS. 11–13, the thickness of the body 54 when considered in directions along a buccolabial-lingual reference axis is non-uniform along the length of the body 54, such that the thickness of the enlarged sections 56 is greater than the thickness of the narrowed sections 58. Other constructions are also possible. For example, the enlarged sections 56 may have a thickness that is equal or substantially equal to the thickness of the narrowed sections 58 in directions along a buccolabial-lingual reference axis. In other words, the body 54 adjacent the notch 60 may have an overall size in a buccolabial-lingual direction that is the same as the length of the minor cross-sectional axis.

With reference to FIG. 13, each of the notches 60 has a certain width in a mesial-distal direction (i.e., in directions along the length of the dental arch, or along the length or central axis of the body 54). The width of the notches 60 is at least as great as the length of the corresponding archwire slots 50 (preferably including the space within the clips 53) so that the narrowed sections 58 can be received in the archwire slots 50. In this manner, the notches 60 serve as receptacles to receive respective brackets 42. Optionally, the width of the notches 60 is greater than the length of the archwire slots 50 in order to enable limited, relative sliding movement of the bracket 42 along the longitudinal axis of the body 54. Alternatively, the width of the notches 60 is substantially equivalent to the length of the archwire slots 50. As an additional option, the width of some of the notches 60 may be substantially equivalent to the length of some of the archwire slots 50, while the width of the remaining notches 60 may be greater than the length of the remaining archwire slots 50. Furthermore, the width of the notches 60 may vary along the length of the arch member 40 in corresponding relation to the variation in width of the respective bracket 42.

In instances where the brackets 42 are to be mounted on or near the mesial-distal center of the respective teeth, the centerline spacing between adjacent notches 60 generally corresponds to the centerline distance between corresponding, adjacent teeth 44 of the dental arch 45. Consequently, the centerline spacing between adjacent notches 60 also generally corresponds to the centerline distance between corresponding, adjacent brackets 42 located on the dental arch 45. In FIG. 13, this centerline spacing between adjacent notches 60 is designated by the letter "d" and preferably is identical or substantially identical to the centerline spacing between adjacent teeth 44. Preferably, this spacing is identical for each of the arch members of the series.

Preferably, the series of arch members including the arch member 40 for a particular patient is selected from an inventory of pre-manufactured arch members 40 that are constructed according to a statistical analysis similar to the analysis described above in connection with the tray 10. For instance, a practitioner may determine the best series of arch members to use from a set of pre-manufactured series of arch members by measuring the width of each of the patient's teeth and then using a numerical analysis to facilitate selection of an optimal pre-manufactured arch member series.

The body 54 of the arch member 40 may be made of any one of a number of suitable materials, including the polymeric materials described above in connection with the tray 10 and the arch member 22 as well as metallic materials. Preferred materials include aesthetic polymers such as translucent, transparent or tooth-colored polymers. Examples of suitable polymers include polycarbonates, polyurethanes, silicones, latex, fluoropolymer and polyolefins. Optionally, fibers such as glass fibers can be embedded in the polymeric material. For instance, short fibers having a length equal to the length of the notches 60 may be placed in the narrowed sections 58 and oriented in a mesial-distal direction. As an additional option, one or more metallic wires can be embedded in the polymeric material, and optionally extend along the entire length of the body 54.

As another option, the body 54 may comprise a shape memory polymer such as "Calo-MER" from the Polymer Technology Group, elastic memory composite ("EMC") from Composite Technology Development, Inc. or "Veriflex" from Cornerstone Research Group ("CRG"). As an example, the body 54 may be made using a shape memory polymer such that the arch member 40 has a shape at room temperature that corresponds to the current shape of the patient's teeth. Once the arch member 40 is placed in the patient's oral cavity and the arch member body 54 rises in temperature to a temperature above its glass transition temperature and to a temperature approximating body temperature, the shape memory characteristics of the polymer cause the arch member 40 to move the teeth to desired positions. Such construction facilitates the initial connection of the arch member 52 to the brackets 54, such as in instances where the initial connection is carried out before the arch member 52 approaches body temperature.

As yet another option, the body 54 may be made of a metallic material such as stainless steel, nitinol or a cobalt-based nickel alloy. As one example, the body 54 may have a coiled configuration similar to the shape of a compression spring to facilitate compression of the body 54 in directions along its longitudinal axis. As another example, the body may comprise multiple strands of metallic wires that are braided or twisted together, with openings that are similar to openings of a compression spring to enable compression of the body 54.

Preferably, the arch member 40 is constructed such that the resiliency of the material of the body 54 provides the desired tooth movement without substantial need for relative sliding movement between the arch member 40 and the brackets 42. For example, the arch member 40 may be constructed so that its shape when relaxed corresponds to the desired shape of the dental arch 45 when all of the teeth 44 have been moved to their intended positions, with the notches 60 being arranged to properly locate each tooth 44 at desired final positions along the dental arch 45. This construction helps to avoid problems that are normally associated with the sliding mechanics observed between conventional archwires and orthodontic appliances, such as friction, bending of the archwire, gouging of the archwire and the like.

The series of arch members including the arch member 40 are used during different stages of an orthodontic treatment program for a particular patient. In particular, the stiffness of the arch members used in the later stages of treatment are stiffer than the arch members used in the earlier stages of treatment. The variation in stiffness may be provided by changing the composition of the arch member, by changing the processing methods used to make the arch member, by changing the shape of the arch member, or by any combination of the foregoing as well as by other methods as well. However, preferably at least some and more preferably all of the arch members in any one series have identical geometries when relaxed. Other aspects of the series of arch members, such as the relative orientation of the couplings or notches 60, are similar to corresponding aspects of the series of trays mentioned above.

All of the patents, patent applications and other publications identified herein are expressly incorporated by reference. Additionally, those skilled in the art will recognize that many modifications and alternative constructions may be made without departing from the essence of this invention. Accordingly, the invention should not be deemed limited to the specific embodiments described in detail above, but instead only by a fair scope of the claims that follow along with their equivalents.

The invention claimed is:

1. A system for moving teeth of a patient's dental arch from an initial tooth arrangement at the beginning of treatment to a final tooth arrangement at the conclusion of treatment comprising a plurality of resilient appliances including an initial appliance for receiving the initial tooth arrangement and a final appliance for receiving the final tooth arrangement, wherein each appliance has a row of spaced apart couplings for connection to respective teeth of the dental arch, wherein each of the couplings of each appliance is arranged in a certain relative orientation with respect to the remaining couplings of the same appliance when the appliance is relaxed, wherein the relative orientation of the couplings is substantially the same for each of the appliances, wherein at least one of the appliances has a stiffness that is greater than the stiffness of at least one other appliance, wherein each appliance comprises an elongated body, wherein the couplings comprise notches, and wherein the body includes a series of narrowed sections adjacent to the notches for reception in respective orthodontic brackets fixed to the patient's teeth.

2. A system for moving teeth according to claim 1 wherein the system includes at least three appliances each having a stiffliess that is different from the stiffness of other appliances of the system.

3. A system for moving teeth according to claim 1 wherein the appliances each have at least one wall section, and wherein the stiffness of the appliances is varied at least in part by changing the thickness of said at least one wall section.

4. A system for moving teeth of a patient's dental arch from an initial tooth arrangement at the beginning of treatment to a final tooth arrangement at the conclusion of treatment comprising a plurality of resilient appliances including an initial appliance for receiving the initial tooth arrangement and a final appliance for receiving the final tooth arrangement, wherein each appliance has a row of spaced apart couplings for connection to respective teeth of the dental arch, wherein the row of couplings of each appliance extends substantially along an arch-shaped curve that is substantially the same for each of the appliances when the appliances are relaxed, wherein at least one appliance has a stiffness that is greater than the stiffness of at least one other appliance, wherein each appliance comprises an elongated body wherein the couplings comprise notches, and wherein the body includes a series of narrowed sections adjacent to the notches for reception in respective orthodontic brackets fixed to the patient's teeth.

5. A system for moving teeth according to claim 4 wherein the row of spaced apart couplings comprises a row of receptacles for receiving respective teeth of the dental arch, and wherein the row of receptacles of at least one appliance includes sufficient receptacles to receive all of the teeth of the dental arch.

6. A system for moving teeth according to claim 4 wherein the curve is an embrasure line.

7. A system for moving teeth according to claim 4 wherein the appliances each have at least one wall section, and wherein the stiffness of the appliances is varied at least in part by changing the thickness of said at least one wall section.

* * * * *

UNITED STATES PATENT AND TRADEMARK OFFICE
CERTIFICATE OF CORRECTION

| | | |
|---|---|---|
| PATENT NO. | : 7,234,936 B2 | |
| APPLICATION NO. | : 10/983457 | |
| DATED | : June 26, 2007 | |
| INVENTOR(S) | : Ming-Lai Lai | |

It is certified that error appears in the above-identified patent and that said Letters Patent is hereby corrected as shown below:

Column 20
Line 22, In Claim 2, delete "stiffliess" and insert -- stiffness --, therefor.

Signed and Sealed this

Twenty-first Day of August, 2007

JON W. DUDAS
*Director of the United States Patent and Trademark Office*